United States Patent [19]

Salter et al.

[11] 4,085,152

[45] Apr. 18, 1978

[54] PRODUCTION OF HEXANITROSTILBENE

[75] Inventors: David Anthony Salter, Sawbridgeworth; Norman Frederick Scilly, Bishop's Stortford; Keith Ellis Watson, Thorverton, near Exeter, all of England

[73] Assignee: The Secretary of State for Defence in Her Britannic Majesty's Government of the United Kingdom of Great Britain and Northern Ireland, London, England

[21] Appl. No.: 760,328

[22] Filed: Jan. 18, 1977

[30] Foreign Application Priority Data

Jan. 22, 1976 United Kingdom .................. 2501/76

[51] Int. Cl.² ...................... C07C 79/10; C07C 76/02
[52] U.S. Cl. .................................................. 260/645
[58] Field of Search .......................... 149/105; 260/645

[56] References Cited

U.S. PATENT DOCUMENTS 3,699,176  10/1972  Syrop .................................... 260/645

*Primary Examiner*—Leland A. Sebastian
*Attorney, Agent, or Firm*—Stevens, Davis, Miller & Mosher

[57] ABSTRACT

In a process for the production of the explosive material 2,2',4,4',6,6'-hexanitrostilbene in which 2,4,6-trinitrotoluene is reacted with an alkali or alkaline earth metal hypochlorite in a solution to precipitate the product, the yield is improved by adding to the mixture, subsequent to commencement of the reaction, a nitrogeneous base. The nitrogeneous base is particularly one having a pKa of 9.25 to 11.25 and an organic amine is especially preferred. The base is added at least 0.5 minute after starting the reaction, and the mixture is stood thereafter for a period which is preferably about 2 hours.

20 Claims, 1 Drawing Figure

U.S. Patent                April 18, 1978                4,085,152
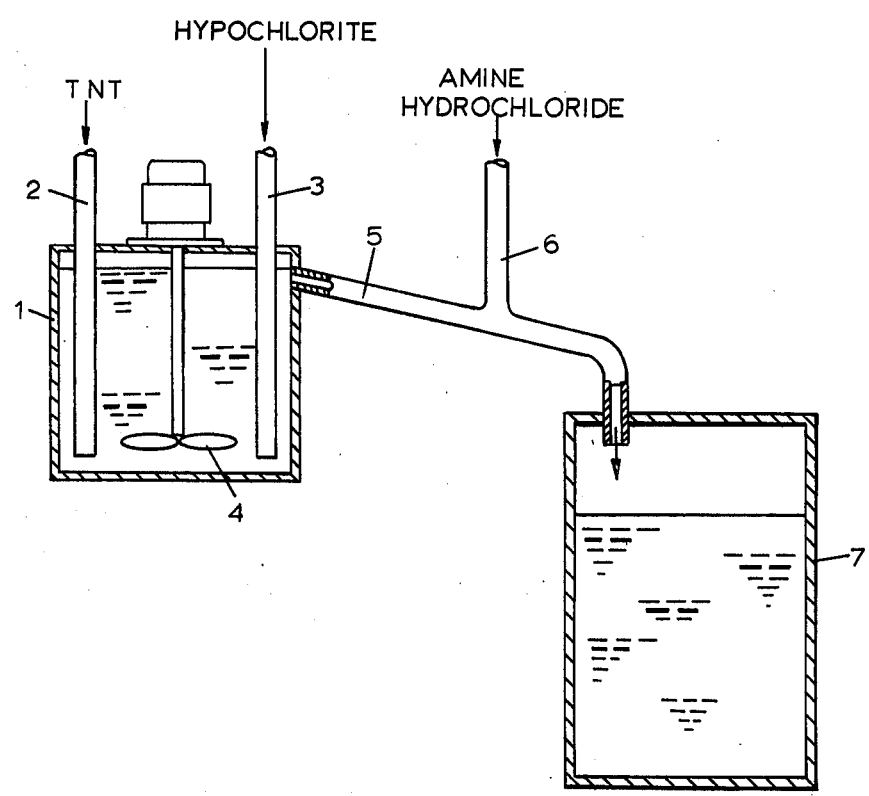

PRODUCTION OF HEXANITROSTILBENE

The invention relates to the production of 2,2',4,4',6,6' - hexanitrostilbene.

2,2',4,4',6,6' - hexanitrostilbene (HNS) has been used as an explosive, but is especially useful as a crystal modifying additive in melt-cast trinitrotoluene (TNT) charges. U.K. patent specification No. 1,249,038 describes and claims this use of HNS.

U.S. Pat. No. 3,505,413 describes the preparation of hexanitrostilbene by the action of sodium hypochlorite on 2,4,6-trinitrotoluene (TNT) at 15° C in tetrahydrofuran/methanol solution. The yield of HNS obtained by this method is typically about 30 to 35% after acetone washing to remove the bulk of co-precipitated impurities, chiefly dipicryl ethane, (the crude yield is generally about 40–45%). In addition to the crude HNS, large amounts of so-called "red oil" (belived to consist chiefly of trinitrobenzyl chloride, trinitrobenzaldehyde, trinitrobenzyl alcohol, trinitrobenzoic acid and trinitrobenzene) are also produced and this greatly complicates the separation of the product and the re-use of the tetrahydrofuran (THF) solvent.

There is therefore a need for a process for the production of HNS from TNT in which the yield of the desired product is increased.

According to the present invention, a process for the production of 2,2',4,4',6,6' - hexanitrostilbene comprises treating 2,4,6-trinitrotoluene with an alkali metal or alkaline earth metal hypochlorite and subsequently adding a nitrogenous base to the mixture. The nitrogenous base, which preferably has a pKa of 9.25 to 11.25, especially 9.75 to 11, as measured in water, may be ammonia but is preferably an organic amine. In order to counteract the alkali or alkaline earth metal hydroxide liberated from the hypochlorite during the reaction it may be advantageous in some cases to add the amine in the form of an amine hydrochloride.

The organic amine may be a primary or secondary amine preferably present in a mole ratio of at least 2:1, especially about 3:1 moles per mole of TNT. There may be an advantage in using a tertiary amine since in this case the maximum yield of HNS is obtained with a lower molar ratio of amine to TNT of about 0.2:1 to 1.5:1, preferably 0.4:1 to 0.5:1 but as the tertiary amines are generally more expensive than either primary or secondary amines the advantage of lower usage may in fact be offset in cost terms. A further slight advantage of using tertiary amines is that the amount of red oil produced is reduced. Suitable tertiary amines include trimethylamine and triethylamine.

As understood in the art, the preferred solvent medium for the reaction of TNT with hypochlorite is a mixture of tetrahydrofuran with an alcohol, preferably methanol or methyl cellosolve, generally in the ratio of 2 volumes of tetrahydrofuran to 1 volume of alcohol. In the case of the process of the present invention it is preferable to carry out the complete process in a tetrahydrofuran-containing solvent.

The hypochlorite is preferably sodium hypochlorite normally added as an aqueous solution.

Generally the process of the invention is carried out by mixing the hypochlorite and a solution of TNT in the tetrahydrofuran-containing solvent at a temperature generally within the range −5° to 25° C and preferably about 10° to 20° C. After a short delay of preferably not less than 0.5 minute and normally not more than 3 minutes, the nitrogenous base is added, conveniently as a solution in water at the same temperature and the mixture allowed to stand for at least half an hour, preferably at least an hour, before filtering off the hexanitrostilbene. Standing periods of up to 2 hours may be advantageous in regard to the yield of HNS which is obtained, but standing for longer periods may cause some loss of yield.

The proces may be conducted either batch-wise or continuously.

The process of the present invention is capable of giving yields of HNS of 45 to 50% or even higher, after acetone washing, in contrast to the prior art processes which give yields of 30 to 35% (after washing).

Specific processes in accordance with the invention will now be described by way of example, with reference to the accompanying drawing which shows in diagrammatic form the apparatus used for a semi-continuous operation.

EXAMPLE 1

15g of TNT dissolved in a mixture of 100 ml tetrahydrofuran and 50 ml methanol at 5° C was added to 100 ml of a well-stirred aqueous solution of sodium hypochlorite at 5° C (7.5% available chlorine ie 7.5 grams per 100 ml), the temperature after addition not being allowed to rise above 15° C. After 1.5 minutes 14.4 ml of a 20% solution of trimethylamine hydrochloride in water (2.87g of the hydrochloride) were added. The mixture was allowed to stand for 1 hour at 15° C and was then filtered. The precipitate was washed with methanol to yield 8.1g of product which on washing with hot acetone was reduced to 7.5g of hexanitrostilbene (50% of theoretical yield).

EXAMPLE 2

The apparatus used was shown diagrammatically in the FIGURE. A solution of TNT (100 g/l) in a 3:2 (v/v) mixture of tetrahydrofuran and methanol was added at a rate of 20 ml/min to a reaction vessel 1 through a first supply pipe 2 reaching to near the bottom of the reaction vessel. An aqueous solution of sodium hypochlorite (7.5% available chlorine) was simultaneously added to the reaction vessel at 13.3 ml/min through a second similar supply pipe 3. The contents of reaction vessel 1 were continuously stirred by a stirrer 4.

Liquid overflowed from the reaction vessel through a transfer pipe 5 positioned to give a working volume within the vessel of 40 ml. The average residence time in the first reaction vessel was thus 1.2 mins.

To the stream of liquid (33.3 ml/min) in overflow pipe 5 was added, through a third supply pipe 6, 1.91 ml/min of a 200 g/l solution of trimethylamine hydrochloride in water. The mixture was then passed into a collecting vessel 7 having a capacity of about 5 liters. (Alternatively the amine hydrochloride solution could have been separately added to the collecting vessel which would then have to have been stirred). After 2 hours the collecting vessel 7 was replaced by a similar vessel and the reaction mixture allowed to stand for one hour before filtering off the product and purifying it as described in Example 1 to give a 50% yield of purified hexanitrostilbene.

EXAMPLE 3

The apparatus used was the same as that described in Example 2.

A solution of TNT (100 g/l) in a 3:2 (v/v) mixture of tetrahydrofuran and methanol was added at a rate of 20 ml/min to the reaction vessel 1 through the first supply pipe 2. An aqueous solution of sodium hypochlorite (7.5% available chlorine) was simultaneously added to the reaction vessel at 13.3 ml/min through the second supply pipe 3. The contents of the reaction vessel were continuously stirred by the stirrer 4, and liquid overflowed from the reaction vessel through the transfer pipe 5 which was positioned to give a working volume within the vessel of 40 ml. The average residence time in the reaction vessel was thus 1.2 mins.

To the stream of liquid (33.3 ml/min) in the overflow pipe 5 was added, through the third supply pipe 6, 1.91 ml/min of a 123 g/l solution of trimethylamine in water. The mixture was then passed into the collecting vessel 7 (capacity about 5 liters) and after 2 hours this collecting vessel was replaced by a similar vessel and the reaction mixture allowed to stand for 1 hour before filtering off the product. Purification of the product as described in Example 1 gave a 43% yield of purified hexanitrostilbene.

I claim:

1. In a process for the production of 2,2',4,4',6,6' - hexanitrostilbene by reaction of a solution of 2,4,6 - trinitrotoluene with an alkali metal or alkaline earth metal hypochlorite to precipitate the product and separation thereof from the solvent, the improvement comprising adding a nitrogenous base to the reaction mixture after commencement of said reaction of 2,4,6 - trinitrotoluene with the hypochlorite.

2. A process according to claim 1, wherein the nitrogenous base has a pka (as measured in water) of 9.25 to 11.25.

3. A process according to claim 2, wherein the nitrogenous base has a pka (as measured in water) of 9.75 to 11.

4. A process according to claim 1, wherein the nitrogenous base is an amine.

5. A process according to claim 4, wherein the amine is a tertiary amine and is used in an amount such that the molar ratio of amine to trinitrotoluene is from 0.2:1 to 1.5:1.

6. A process according to claim 5, wherein the tertiary amine is used in an amount such that the molar ratio of amine to trinitrotoluene is from 0.4:1 to 0.5:1.

7. A process according to claim 5, wherein the tertiary amine is trimethylamine.

8. A process according to claim 5, wherein the tertiary amine is triethylamine.

9. A process according to claim 4, wherein the amine is a primary or secondary amine and is used in an amount such that the molar ratio of amine to trinitrotoluene is at least 2:1.

10. A process according to claim 9, wherein the primary or secondary amine is present in an amount such that the molar ratio of amine to trinitrotoluene is about 3:1.

11. A process according to claim 4 wherein the amine is added in the form of the corresponding hydrochloride.

12. A process according to claim 1, wherein the hypochlorite is added as a freshly prepared aqueous solution of sodium hypochlorite.

13. A process according to claim 1 wherein the nitrogeneous base is added to the reaction mixture of the trinitrotoluene with the hypochlorite at least 0.5 minute after forming the mixture.

14. A process according to claim 13, wherein the nitrogeneous base is added not more than 3 minutes after forming the mixture.

15. A process according to claim 1 wherein, after addition of the nitrogenous base, the mixture is allowed to stand for at least 30 minutes before filtering off the product.

16. A process according to claim 15, wherein the mixture is allowed to stand for up to about 2 hours.

17. A process according to claim 1, wherein the temperature is from 10° to 20° C.

18. A process according to claim 1, wherein the reaction is carried out in a tetrahydrofuran-containing solvent.

19. A process according to claim 18, wherein the solvent comprises a mixture of tetrahydrofuran and an alcohol.

20. In a process for the production of 2,2,4',4',6,6', - hexanitrostilbene by the reaction of 2,4,6- trinitrotoluene in a tetrahydrofuran-containing solvent with an alkali metal hypochlorite to precipitate the product and separation thereof from the solvent, the improvement comprising adding an organic amine to the reaction mixture after commencement of said reaction of 2,4,6 - trinitrotoluene with the hypochlorite.

* * * * *